United States Patent [19]
Austin et al.

[11] Patent Number: 5,405,336
[45] Date of Patent: Apr. 11, 1995

[54] CONNECTOR FOR CATHETER SYSTEM

[75] Inventors: Jon W. Austin, Phoenix; James R. Pluth; Barry A. Cassidy, both of Scottsdale, all of Ariz.

[73] Assignee: Mayo Foundation for Medical Education & Research, Minn.

[21] Appl. No.: 102,303

[22] Filed: Aug. 5, 1993

[51] Int. Cl.⁶ .......................................... A61M 25/00
[52] U.S. Cl. ................................................ 604/280
[58] Field of Search .............. 604/99, 100, 103, 111, 604/243, 283, 905, 326; 285/1, 7, 8, 93, 260

[56] References Cited

U.S. PATENT DOCUMENTS

| | | | |
|---|---|---|---|
| 2,701,147 | 2/1955 | Summerville | 285/1 |
| 3,181,895 | 5/1965 | Cator | 285/1 |
| 3,731,684 | 5/1973 | Spiegel | 604/326 |
| 3,951,153 | 4/1976 | Leucci | 604/100 |
| 4,067,329 | 1/1978 | Winicki | 285/93 |
| 4,256,106 | 3/1981 | Shoor | 604/905 |
| 4,369,781 | 1/1983 | Gilson et al. | 604/905 |
| 4,473,369 | 9/1984 | Lueders et al. | 604/283 |
| 4,692,150 | 9/1987 | Cianci et al. | 604/111 |
| 4,828,554 | 5/1989 | Griffin | 604/326 |
| 5,152,555 | 10/1992 | Szabo | 285/93 |

Primary Examiner—John D. Yasko
Assistant Examiner—Manuel Mendez
Attorney, Agent, or Firm—Gregory J. Nelson

[57] ABSTRACT

A multiple section connector for a catheter drainage tube employed with the body which connector will break away or separate when a predetermined pulling or traction force is applied. The sections are joined having a predetermined frictional engagement. The invention may include a protective expandable sheath to maintain sterility. A check valve may be inserted in the tubing to restrict flow through the tubing to one direction.

19 Claims, 2 Drawing Sheets

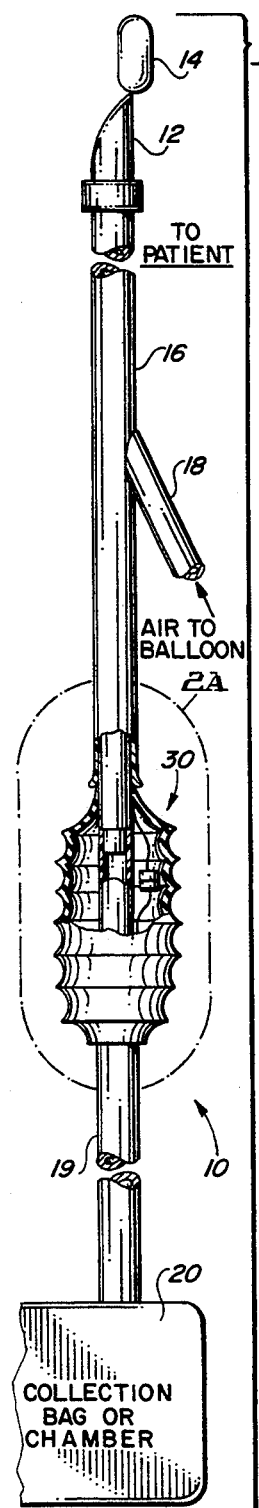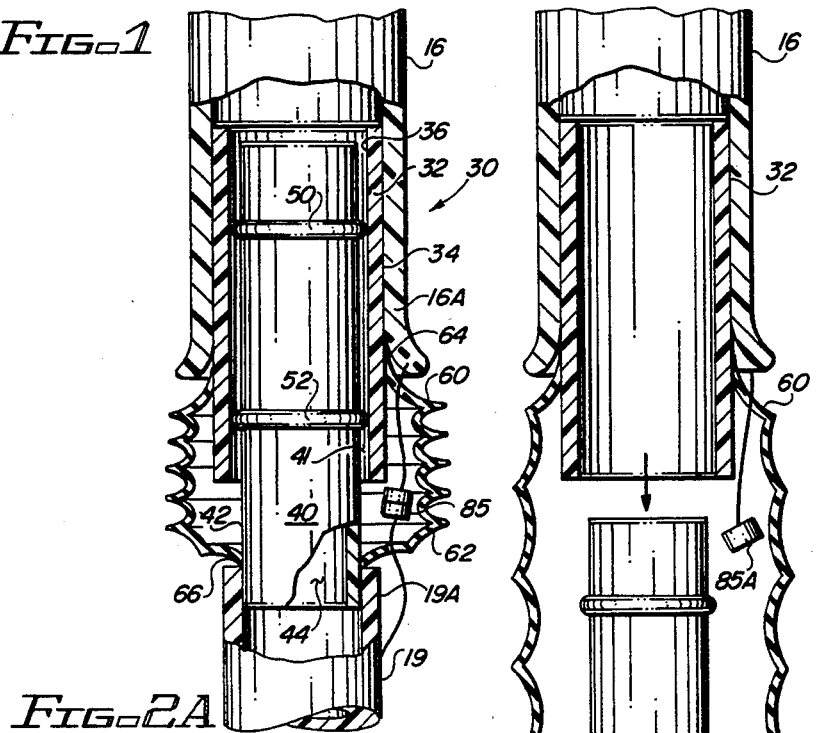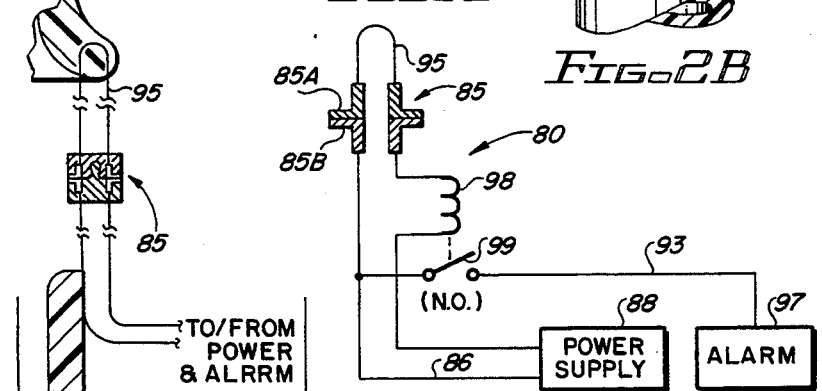

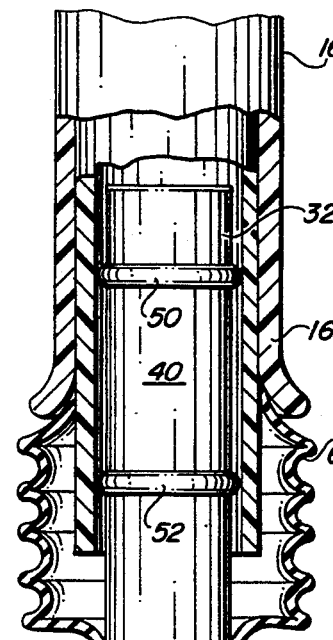
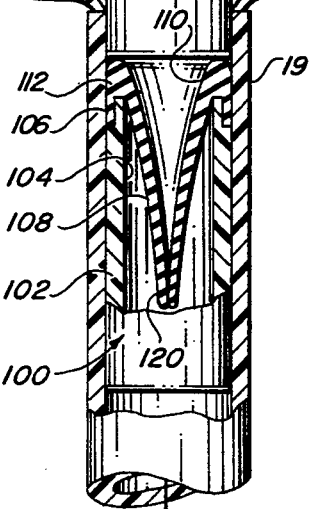
FIG.7
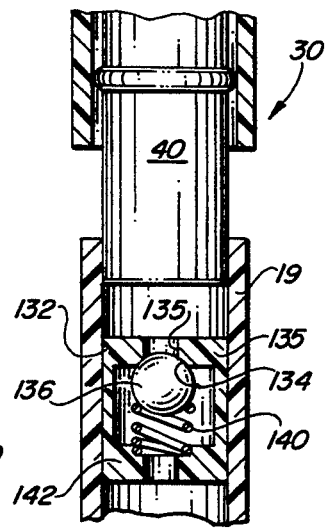
FIG.8
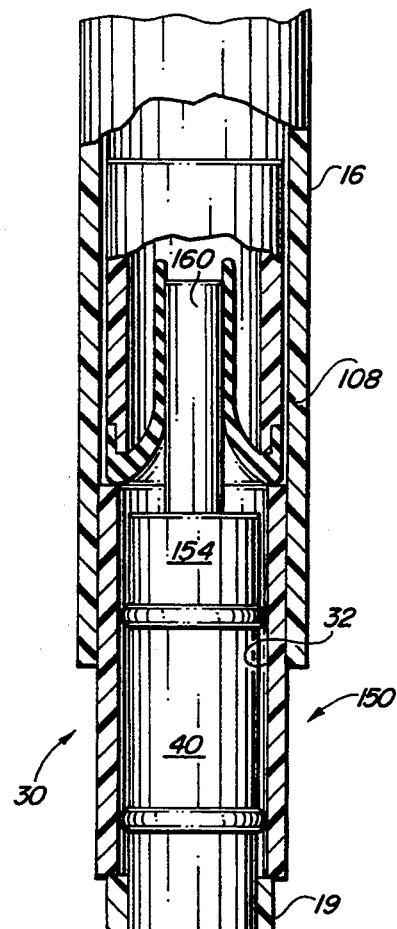
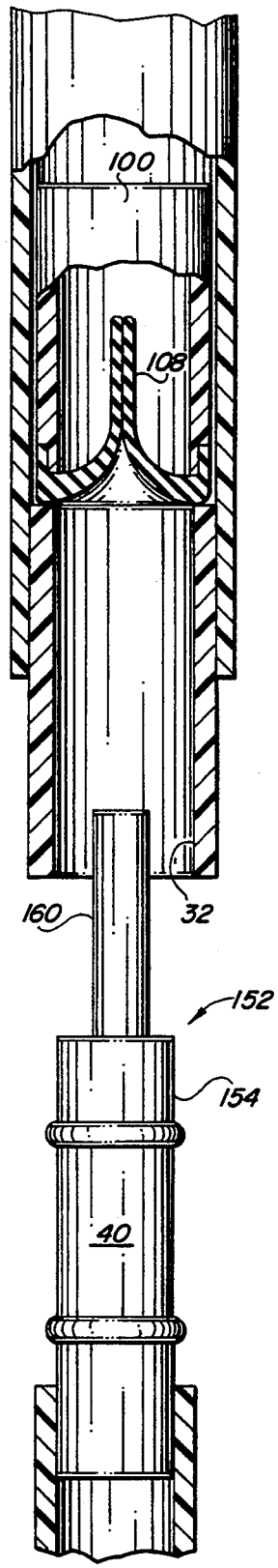
FIG.9A  FIG.9B

CONNECTOR FOR CATHETER SYSTEM

FIELD OF INVENTION

The present invention generally relates to medical fluid systems and more particularly relates to a connector for catheter systems which connector is placed in the external tubing line and which will break away or uncouple to prevent dislodgement of the indwelling catheter. This serves to protect the patient from potential injury were the catheter to become dislodged or when excessive tension is placed on the external tubing line.

It is common medical practice, particularly with patients who have the inability or experience difficulty in urinating, to drain urine from the patient's bladder through a catheter system. The conventional catheter system includes a catheter which is positioned in the urethra which catheter is connected to a flexible tubing or a conduit which runs external to the patient to a collection container or bag. The tube is generally four to six feet in length to allow the patient some limited movement and mobility. Generally the collection container is suspended at an elevation below the patient. The typical indwelling type of urinary catheter system includes an elastomeric tube with a catheter end that is inserted through the urethral orifice and passed upwardly into the urinary bladder. The indwelling urinary catheter is unique in that a balloon is attached to the tip of the catheter. Once the catheter is inserted into the patient's bladder, the balloon is inflated by injecting air, sterile water or saline solution into the balloon through a special Y-site located along the tubing. A seal exists at an inflation port at the balloon to prevent the air, sterile water or saline solution from leaking out allowing the balloon to deflate. When inflated, the balloon rests on the wall of the bladder and is significantly larger than the diameter of the internal sphincter of the bladder or the urethra. Consequently, the catheter remains inside the bladder providing a conduit for continuous drainage of the bladder to the collection container.

Removal of the indwelling urinary catheter is accomplished by draining the air, sterile water or saline solution from the inflated balloon. This is done by either cutting the inflation port proximal to the seal or by withdrawing the saline or water with a syringe.

Indwelling urinary catheters and other types of catheters used in medical and surgical procedures can be accidentally dislodged if sufficient force is applied to either the indwelling catheter or the long tubing extending to the collection container. Since the external tubing is long and bulky, it can easily be stepped on or pulled on by the patient, medical attendant or visitor. The tubing can also be caught in the bed or other fixture, resulting in painful trauma from the dislodgement or pulling of the catheter. In some cases pulling of the catheter can result in serious damage to the bladder, prostate and/or urethra.

A typical situation occurs when a patient is being moved from a bed to a chair and the care giver inadvertently steps on the external tubing extending to the collection container. When the patient moves or attempts to sit down, the length of the tube extending from the patient becomes taut and the traction on the catheter will pull the inflated balloon out of the bladder and through the urethra.

Another potentially harmful situation occurs when the tubing to the collection container is draped over the side of a bed or chair and rests on the floor. The long tubing is easily caught on a person's foot or on adjacent equipment such as a portable X-ray machine, ultrasound machine or other fixture that may be in the area. When the person moves or the fixture is moved, the tubing is pulled and the inflated balloon may become dislodged from the bladder causing pain and possible injury to the patient.

The problem of a dislodged catheter may also divert medical attention from other more critical procedures increasing the cost and risk to the patient.

DESCRIPTION OF THE PRIOR ART

Various urine drainage catheter systems can be found in the prior art. For example, U.S. Pat. No. 3,699,964 shows a closed urinary drainage and irrigation system having a catheter adapted to provide a valve for alternately irrigating the bladder and draining the bladder through the drainage tube. The patent also shows a one-way ball valve and housing at the end of the drainage tube to prevent reflux while preventing flee-flow of urine through the drainage tube into the collection bag.

U.S. Pat. No. 3,768,476 shows a connector/adaptor for use in an irrigation drainage system having male and female coupling members, one adapted for connection to a catheter and the other adapted for connection to the drainage bag. The coupling members are linked by a flexible plastic strap so that when decoupled, the members remain linked.

U.S. Pat. No. 4,029,099 shows a urinary catheter device having a flexible tube connected to a collection container. The device is intended to prevent painful trauma as a result of the pulling of the catheter from the bladder. This is accomplished by a bellows or accordion-like construction which expands and contracts to a limited length.

As is apparent from the foregoing and from a review of the prior art in general, there are various catheter drainage devices which deal with the problem of the inadvertent and unintentional dislodgement of the catheter from the bladder and the problem of migration of infectious microorganisms from the collection bag through the tubing to the patient. However, despite the existence of these devices, there nevertheless exists a need for an improved catheter system which will protect the patient against unintentional dislodgement of the catheter.

Accordingly, it is a broad object of the present invention to provide a catheter system which protects the patient from possible pain and injury due to tensile or traction force applied to the external tubing which would tend to withdraw or dislodge the catheter, be it a urinary catheter or other type of catheter, from the patient.

BRIEF SUMMARY OF THE INVENTION

Briefly, this broad object is achieved in accordance with the present invention by a connector device inserted in the external drainage tubing line which will break away or separate when a predictable or predetermined force is applied to the tubing. In a basic embodiment, the connector consists of two sections, a first section which is in the form of a rigid or semi-rigid sleeve which is inserted into a section of the tubing leading film the patient to the catheter. The first section defines an internal passageway. A generally cylindrical coupling section defines an interior flow path and has its distal end attached to or inserted to the tubing leading to the collection connector. The exterior of the coupling member is configured so as to have a predetermined frictional engagement with the internal passageway of the sleeve. In a preferred embodiment, frictional engagement is achieved by providing one or more O-rings extending about the exterior surface of the coupling section. The external diameter of the O-rings is slightly larger than the internal diameter of the passageway in the sleeve. An abrupt traction force applied to the tubing as the result of the tubing being pulled will result in the coupling being pulled from the sleeve dislodging the coupling sections. The frictional resistance is specifically selected so the dislodgement occurs prior to a force magnitude that would cause dislodgement of the catheter at the end of the tubing. The desired frictional resistance is obtained by use of component materials selected for their frictional characteristics as well as strength, sterility and medical acceptability.

In addition, the invention comprehends a protective expandable sheath which extends about the connector section so that in the event the connector section becomes uncoupled, the integrity of the system remains intact and sterile.

A further aspect of the invention comprehends the addition of a check valve or flutter valve which may be included to allow the fluid to travel through the system in only one direction to reduce the possibility of microorganisms passing from the drainage bag to the patient and also to close off the tubing at the coupling in the event the coupling or connector becomes uncoupled.

The present invention can be incorporated into any catheter drainage system employed with the body, for example, jejunostomy, common duct drainage, and even chest drainage tubes, when the latter are connected across a one-way check or flutter valve.

In addition, catheters and cannulae are often placed in blood vessels for fluid administration, access to blood samples, monitoring blood pressure and drainage of blood. Accidental dislodgement of such blood access catheters can lead to a number of problems including, but not limited to, loss of blood, hematoma, injection site trauma, and contamination of the catheter system.

The above and further objects and advantages and features of the present invention will become more apparent from the following description, claims, taken along with the accompanying drawings in which:

BRIEF DESCRIPTION OF THE DISCLOSURE

FIG. 1 is an elevational view of a closed drainage catheter system embodying the connector of the present invention;

FIG. 2A is a detail view, partly in section, of the connector as shown in FIG. 1 with the components in a connected condition;

FIG. 2B is a detail view similar to 2A showing the catheter system uncoupled or disconnected;

FIG. 3 is a detail view showing a portion of the disconnect alarm system which indicates an uncoupled condition;

FIG. 4 is a detail view of the electrical connector in the disconnect alarm system;

FIG. 5 is a schematic of the disconnect alarm system;

FIG. 6 is a detail view, partly in section, of another embodiment of the connector:

FIG. 7 is a detail view, partly in section, showing an alternate embodiment of the present invention which embodiments include a one-way flutter or check valve;

FIG. 8 is a detail view, partly in section, of another type of check valve shown in the connector system;

FIG. 9A is a detail view partly in section, showing another embodiment of the connector of the present invention in a closed position including a flow nozzle adapted to maintain a one-way check valve in an open position until the coupling is disconnected;

FIG. 9B is a view similar to FIG. 9A showing the connector disconnected and the check or flutter valve in a closed position to prevent drainage from the patient.

DETAILED DESCRIPTION OF THE INVENTION

Turning now to FIG. 1, a typical drainage catheter system 10 is shown which has a catheter 12 at its upper proximal end for insertion into the body of the patient. The catheter 12 may be any type of catheter but is shown as an indwelling catheter having an inflatable balloon member 14 at its tip. The catheter is connected to an upper length of flexible tubing 16. Located at a selected location along tubing length 16 is a Y-site or port 18 which allows air, sterile water or saline to be introduced into the inflatable balloon 14. The lower section 19 of the drainage tubing 16 is connected at its lower end to a receptacle or collection container 20. The collection container preferably is a flexible plastic bag that is expansible and as it is filled with fluid will not create any back pressure. The container may be periodically removed and emptied or replaced with a new collection container. The entire system should be leak proof so that fluid cannot leak from the system and contamination cannot enter into the system.

The particular catheter drainage system shown and described above is representative and as indicated is an indwelling type of catheter having expansible balloon at its end to retain the catheter in position. It is to be understood that as used herein "catheter" is broadly defined meaning various medical fluid systems and, accordingly, the connector of the present invention may be used with various types of medical catheter systems. The particular catheter system forms no part of the present invention. Various types of catheter systems in which the invention may be employed include jejunostomy, common duct drainage and chest drainage systems, blood and I.V. systems.

As shown in FIG. 1, the separable connector of the present invention is generally designated by the numeral 30 and is located at a selected intermediate location in the drainage between tubing sections 16 and 19 at ends 16A and 19A. Preferably, the connector is inserted into the distal end of the catheter. In a typical arrangement the overall length of the tubing sections 16, 19 may be as much as 4' to 6'. The connector 30 consists of a sleeve 32 which is generally cylindrical having an outer surface 34 and defining an interior 36. The outer diameter of the sleeve is selected so the sleeve may be snugly inserted into the distal end portion 16A of drainage tubing section 16. Preferably the sleeve is fabricated from a suitable medical grade plastic such as PVC and is also preferably transparent or translucent. The sleeve should have sufficient rigidity to allow it to be easily inserted into the tubing section extending inward from the distal tubing end 16A.

Coupling section 40 is generally tubular having an outer generally cylindrical surface 42 and defines an internal flow passageway 44. The internal diameter of tubing section 19 is somewhat less than the diameter of adjacent tubing section 16. Accordingly, the coupling section 40 is configured having an outer diameter which allows it to be snugly inserted partway into end 19A of tubing section 19. It may be desirable in some cases to permanently secure the coupling 40 and tubing section 19 by suitable means such as by an adhesive or by sonic welding or by other techniques well known to those in the art. The outer diameter of coupling 40 is also selected so as to be less than the internal diameter of the sleeve providing an annular clearance area 41 between the two.

The outer surface of the coupling section projecting beyond the terminus or end of tubing section 19A is configured to allow the sleeve to engage the coupling section with predetermined frictional resistance. In a preferred embodiment, the frictional resistance is achieved by one or more O-rings 50 and 52 at axially spaced-apart locations extending circumferentially about the coupling. The O-rings are preferably a medical grade silicon, urethane, latex rubber or other elastomeric material and when the coupling is inserted into the sleeve, a separation force in the range of ½# to 5# is required to separate the coupling section and sleeve. In other embodiments, as seen in FIG. 6, the annular projections may be in the form of axially extending ribs 51 formed in the exterior of the coupling section. The axial or annularly extending projections may also be formed or molded integrally on the exterior coupling surface. O-ring 50 assists to prevent leakage around the coupling section 40. The projections may also be formed on the interior of the sleeve with the outer diameter of the coupling section being smooth. Alternatively, cooperating projections may be formed on both the coupling section and sleeves. The materials of the sleeve and coupling section may also be selected to provide a predetermined frictional engagement so that a predictable separation force will cause the components to uncouple. The connector 30 when assembled as shown in FIG. 2A defines a sealed fluid path from the catheter 12 to the collection container 20 located at the distal end of the drainage system. The O-rings or other projections prevent leakage of fluid flow between the sleeve and coupling sections. The coupling section 40 may be color coded, that is, provided in a highly visible color so that separation of the coupling components is easily determined by visual inspection.

To insure the integrity of the system and to prevent leakage and contamination, even in the event the connector becomes decoupled, an expandable sheath 60 extends around and along the connector between the sleeve and coupling sections. The sheath has a body 62 which has one end 64 which attaches to the sleeve 32 inward from its end and is bonded to the sleeve by any suitable means shown as a bead 65 which may be adhesive or may be formed by sonic welding methods. The opposite end 66 of the sheath 62 is sealed to the coupling section 40. In this manner, the sheath houses and encloses the connector.

The body 62 of the sheath 60 may be formed of any suitable fluid impervious such as medical grade flexible plastic material such as polyvinyl chloride and is preferably transparent or translucent to assist the attending medical personnel in viewing the enclosed connector.

The body 62 is formed so that it is axially extendable or expandable and to this end is shown as being formed having a series of bellows-like folds 66. The bellow-like folds permit the sheath to assume a normal contracted position about the connector as shown in FIG. 2A.

Upon the application of an axial traction force which causes the connector sections to become disconnected as shown in FIG. 2B, the axial length of the sheath 60 expands maintaining the integrity of the system when uncoupling occurs. The particular configuration of the expandable sections may be of a bellows-like construction as described or any folded construction which permits the overall length of sheath to be extended. In some instances, an elastomeric sheath material could be used in lieu of the bellows-like construction shown which would stretch to accommodate separation.

It will be apparent from the foregoing that in the event the tubing becomes caught or entangled in some manner and as a result an axial traction force is applied to the tube, the force will cause the connector to become uncoupled between the sleeve 32 and the coupling section 40 as seen in FIG. 2B. Uncoupling will occur before the traction force is sufficient to dislodge the catheter from the patient and causing undue pain and physical damage to the patient. In the event the connector uncouples or disconnects, it is a relatively simple procedure to remove the existing connector and replace it with a new connector.

It is possible that the uncoupling of the catheter connector may occur at a time when there is no medical attendant present. Accordingly, it is desirable to have some type of alarm which will provide either a visible or audible signal to medical personnel. As such, the audible or visible signal could be emitted at bedside or at a remote station to alert medical personnel to check on the condition of the patient.

Accordingly, referring to FIGS. 1 to 5, the connector system of the present invention includes such an alarm which is indicated by the numeral 80. The alarm system 80 includes an electrical connector 85 and conductor 86 extends from power supply 88 to male connector section 85B of the electrical connector. The conductor 86 terminates at contact 90. The connector 85A is provided with a projection 92 which is received in the receptacle 93 of female connector section 85A. Female connector section 85A has a contact 90A which, when the connector halves are assembled, is in electrical contact with contact 90. Conductor 95 extends from contact 90A to contact 94A of the female conductor. Contact 94A is in electrical contact with contact 94 in the male connector section. As seen in FIG. 5, when the electrical connector sections are assembled and power supplied via conductors 86 and 95, solenoid 98 is energized so that switch 99 is in the normally opened position. When the sections 85A and 85B of the electrical connector are separated, switch 99 will close energizing alarm 97. The portions of the electrical connector will become separated when the connector 30 separates as shown in FIG. 2B inasmuch as section 85A is tethered by conductor 95 to the upper tubing section 16 and the opposite electrical connector portion 85B is tethered by conductor 86 to the lower tubing section 19. When this occurs, an alarm is activated as the closed-off switch 99 will energize the alarm 97 via conductor 93. The alarm signal may be bedside or may be transmitted to a remote medical station.

FIG. 7 shows another embodiment of the present invention. In this embodiment, as well as in the description of other embodiments, the same or similar elements as described above have been identified with the same reference numeral. In the embodiment shown in FIG. 1, the distal end 16A upstream section of the drainage tubing 16 is shown receiving cylindrical sleeve 32 in a snug fit. The downstream section 19 of the drainage tube receives the coupling section 40 which is shown having annular O-ring members 50 and 52 extending about its surface which members engage the interior of the sleeve 32 with predetermined frictional engagement. As has been described above, application of a predetermined traction force to the tubing will cause the sleeve and coupling to separate prior to causing dislodgement of the catheter at the upper end of the set.

In FIG. 7, a check valve 100 is inserted in the downstream tubing line 19 downstream of the connector. The check valve 100 has a generally cylindrical body 102 which is snugly inserted into the downstream tubing section 19 and may be secured to the tubing by suitable methods, such as by adhesives or by sonic welding methods. The body 102 defines an axially extending flow passageway 104. The upper end of the body is shown as having an annularly extending groove 106 which engages a portion of the valve closure member 110. The valve closure member 110 consists of an annular flange member 112 which has an outer lip engageable about the annular groove at the upper end of the body. The valve closure member further includes an inwardly diverging section 108 which is generally conical. The valve closure member is preferably fabricated from a suitable elastomeric material such as a medically-acceptable latex rubber. The valve member has a normally closed condition as shown in FIG. 7 so that it serves as a one-way check valve so that fluid flow will pass through the valve only in the direction indicated by the arrow causing the lower seating edges 120 of the valving closure member to separate. Fluid flow in the reverse direction will be prevented by the valve. Thus, the valve in the normal operating condition will prevent migration of fluid and/or impede migration of microorganisms from the collection bag to the patient via the drainage tube and catheter. The sheath 60 is partially shown for clarity and expandably encloses the connector as has been described above.

FIG. 8 illustrates another form of check valve associated with the connector. The check valve 130 is disposed in the tubing section 19 downstream of coupling section 40 of the connector 30. The check valve has a body 132 defining a valve seat 134 through which extends port 136. A ball 136 is normally held in engagement with valve seat 134 by spring 140 which is retained by flange 142. Flow in the direction of the arrow will cause the ball to unseat permitting one-way flow.

Referring to FIGS. 9A and 9B, another embodiment of the present invention is shown generally designated by the numeral 150 and in which elements the same or similar to elements previously described are indicated by the same numerals. The connector 30 again is positioned between an upstream tubing section 16 and a downstream tubing section 19. The connector 30 includes sleeve 32 and a coupling section 40 which are engaged in the assembled position and frictionally restrained so that a predetermined tensile force will cause the components to predictably separate. FIG. 9A illustrates the connector in the assembled position which allows fluid flow passing to the collection container in the direction of the arrow. A sheath 60 may enclose the connector but is omitted for clarity.

A check valve 100 as described with reference to FIG. 7 is shown installed in the upstream tubing section upstream of the edge of this section. The valve has a flexible closure member 108 which is fabricated from an elastomeric member with memory which tends to assume the closed position. The check valve 100 is positioned to shut off drainage flow from the patient in the event the connector uncouples which, if the connector does not include a sheath, will protect against soiling of the patient and bed clothes.

To maintain the check valve 100 in an open position in the normal operating position, the upstream end of the connector is provided with a flow nozzle 152. The flow nozzle has a cylindrical cap 154 which is secured to the end of the coupling 40 by use of a suitable adhesive or by frictional engagement. An axially extending hollow tube or stem 160 extends from the cap and communicates the flow passage in the coupling section 40 with the upstream tubing to establish a flow path. In the coupled position as shown in FIG. 9A, the stem 160 has sufficient length to extend into the valving member holding the valving closure member 108 in an open position.

Upon separation of the connector due to the application of traction force to the tubing, the sleeve and coupling will uncouple withdrawing the tube or stem of the flow nozzle from the valving member. The valving closure member 108 will then assume its closed position as shown in FIG. 9B preventing flow of fluid from the upstream drainage tubing section.

From the foregoing it will be obvious that the present invention provides a unique and effective connector for catheter drainage systems of various types which catheter will prevent excessive pulling or traction force from being transmitted to the catheter and patient.

The device is simple, effective and lends itself to manufacturing techniques which make it an economically feasible disposable item. The various accessories such as the protective sheath and alarm are optional.

It will be obvious to those skilled in the art to make various changes, alterations and modifications to the connector system described herein. To the extent such changes, alterations and modifications do not depart from the spirit and scope of the appended claims, they are intended to be encompassed therein.

We claim:

1. A drainage system for draining fluids from the body of a patient to a collection container, said system comprising:

(a) an upstream tubing section attachable to the body at a second end and having an opposite first end;

(b) a downstream tubing section connectable to the collection container at a second end and having an opposite first end;

(c) a sleeve insertable in one of said tubing section's first end, said sleeve defining an internal flow passageway;

(d) a coupling section securable to the other of said tubing section's first end, said coupling section having an external surface engageable in said internal flow passageway in predetermined frictional engagement therewith whereby a traction separating force of a predetermined magnitude will cause said sleeve and coupling to separate; and (e) alarm means for emitting an alarm upon separation of said sleeve and coupling section, said alarm means including a power supply, an electrical circuit connected to an alarm and a connector in said electrical circuit, said connector being attached to said sleeve and coupling section and being separable when said sleeve and coupling section separate to actuate said alarm means.

2. The system of claim 1 further including a protective sheath extending between said sleeve and coupling section.

3. The system of claim 2 wherein said sheath is expansible and collapsible.

4. The system of claim 3 wherein said sheath is clear flexible plastic.

5. The system of claim 1 wherein said alarm is an audible alarm.

6. The system of claim 1 wherein said alarm is a visible alarm.

7. The system of claim 1 wherein said drainage system is a urinary indwelling catheter system and further including an indwelling catheter having a flow passage engageable with the second end of said upstream tubing section.

8. The drainage system of claim 1 wherein one of said sleeve and coupling sections is color coded to provide a visual indication upon separation.

9. The drainage system of claim 1 wherein said coupling section is provided with a projection on the said external surface.

10. The drainage system of claim 9 wherein said sleeve is plastic and said projections comprise at least one annular O-ring selected from the group of materials consisting of silicon, urethane and latex rubber.

11. The drainage system of claim 1 wherein said predetermined frictional engagement is approximately between ½ to 5 pounds.

12. An in-line connector for a fluid system which system includes a catheter insertable into the body of a patient, a fluid container and an upstream tubing section and a downstream tubing section, the upstream tubing section being connectable to said catheter at a second end and having an opposite first end and a downstream tubing section attachable to said fluid container at a second end and having an opposite first end, said connector comprising:

(a) a sleeve insertable in one of said first tubing ends, said sleeve defining an internal flow passageway; and (b) a coupling section securable to the other of said first tubing ends, said coupling section having an external surface engageable in the said flow passageway in predetermined frictional engagement therewith, the magnitude of said frictional engagement being less than the traction force required to dislodge the said catheter from the patient, whereby a traction force of predetermined magnitude will cause said sleeve and coupling section to uncouple prior to dislodgement of the catheter preventing possible injury to the patient.

13. The connector of claim 12 wherein one of said flow passageway and said external surface includes at least one circumferentially extending O-ring.

14. The connector of claim 13 wherein said O-ring is selected from a group of materials consisting of silicon, urethane or latex rubber.

15. The connector of claim 14 further including a flexible sheath extending between said sleeve and coupling section.

16. The connector of claim 12 further including alarm means for emitting an alarm upon uncoupling of said sleeve and coupling sections.

17. The connector of claim 12 wherein one of said sleeve and coupling sections is provided with indicia to provide a visual indication upon separation.

18. The connector of claim 12 wherein said sleeve and coupling sections are of different materials.

19. The connector of claim 12 wherein one of said flow passageway and said external surface is provided with projections.

* * * * *